(12) United States Patent
Mahe et al.

(10) Patent No.: US 7,662,401 B2
(45) Date of Patent: Feb. 16, 2010

(54) ADMINISTRATION OF EXTRACTS OF NONFRUITING NONPHOTOSYNTHETIC FILAMENTOUS BACTERIA FOR INCREASING THE ENDOGENOUS SYNTHESIS OF SUPEROXIDE DISMUTASE

(75) Inventors: Yann Mahe, Morsang sur Orge (FR); Alain Meybeck, Courbevoie (FR)

(73) Assignee: L'Oreal, Paris (FR)

( * ) Notice: Subject to any disclaimer, the term of this patent is extended or adjusted under 35 U.S.C. 154(b) by 34 days.

(21) Appl. No.: 11/798,849

(22) Filed: May 17, 2007

(65) Prior Publication Data

US 2007/0237746 A1    Oct. 11, 2007

Related U.S. Application Data

(62) Division of application No. 10/408,357, filed on Apr. 8, 2003, now abandoned.

(60) Provisional application No. 60/371,715, filed on Apr. 12, 2002.

(30) Foreign Application Priority Data

Apr. 8, 2002  (FR) .................................. 02 04339

(51) Int. Cl.
*A61K 35/66* (2006.01)
*A61K 35/74* (2006.01)
*A61K 36/76* (2006.01)
*A61K 39/00* (2006.01)

(52) U.S. Cl. .................................. 424/282.1; 424/115

(58) Field of Classification Search ................. 424/115, 424/282.1
See application file for complete search history.

(56) References Cited

U.S. PATENT DOCUMENTS

| | | | | |
|---|---|---|---|---|
| 5,597,558 A | * | 1/1997 | Aubert et al. | 424/70.1 |
| 5,618,521 A | * | 4/1997 | de Rigal et al. | 424/59 |
| 5,795,574 A | * | 8/1998 | Breton et al. | 424/115 |
| 6,190,671 B1 | * | 2/2001 | Aubert et al. | 424/282.1 |
| 6,242,229 B1 | * | 6/2001 | Pineau et al. | 435/170 |
| 6,316,012 B1 | * | 11/2001 | N'Guyen et al. | 424/401 |

* cited by examiner

*Primary Examiner*—Johann R Richter
*Assistant Examiner*—Courtney Brown
(74) *Attorney, Agent, or Firm*—Buchanan, Ingersoll & Rooney P.C.

(57) ABSTRACT

The present invention relates to the cosmetic or pharmaceutical use of an extract of a nonfruiting nonphotosynthetic filamentous bacterium in a composition containing a cosmetically or pharmaceutically acceptable medium, as an agent increasing the endogenous synthesis of superoxide dismutase, in particular for preventing and/or limiting the formation of free radicals and/or removing the free radicals present in cells; in addition, the invention relates to a composition comprising at least one extract of *Vitreoscilla filiformis* and lycopene.

9 Claims, No Drawings

ADMINISTRATION OF EXTRACTS OF NONFRUITING NONPHOTOSYNTHETIC FILAMENTOUS BACTERIA FOR INCREASING THE ENDOGENOUS SYNTHESIS OF SUPEROXIDE DISMUTASE

CROSS-REFERENCE TO PRIORITY/PROVISIONAL APPLICATIONS

This application claims priority under 35 U.S.C. § 119 of FR-02/04339, filed Apr. 8, 2002, and of provisional application Ser. No. 60/371,715, filed Apr. 11, 2002, both hereby expressly incorporated by reference. This application is also a continuation of said '715 provisional.

BACKGROUND OF THE INVENTION

1. Technical Field of the Invention

The present invention relates to the cosmetic or pharmaceutical use of an extract of a nonfruiting (nonfructifying) nonphotosynthetic filamentous bacterium in a composition containing a cosmetically or pharmaceutically acceptable medium, as an agent increasing the endogenous synthesis of superoxide dismutase (SOD), in particular for preventing and/or limiting the formation of free radicals and/or removing the free radicals present in cells.

2. Description of the Prior Art

Over time, various signs appear on the skin which are very characteristic of aging, resulting in particular in a modification of the structure and functions of the skin.

This aging, which is of a physiological nature, results from the action of two main classes of components, an endogenous component resulting in particular from the natural production of superoxide ions, in particular produced during cell respiration. The other component is exogenous. Indeed, aging may be accelerated by environmental factors such as repeated exposure of the skin to sunlight, and in particular to ultraviolet A radiation, to pollution, in particular to diesel particles and to cigarette smoke.

It is known that the toxicity of atmospheric pollutants, in particular of gaseous pollutants such as sulphur dioxide, ozone and nitrogen oxides on the constituents of the skin (fibers, cells, enzymes) and on the sebum secreted by the skin is linked in particular to their free radical initiating activity, a source of oxidation phenomena which cause cellular damage in living beings.

Living cells, which are in direct and permanent contact with the external medium (in particular the skin, the scalp and certain mucous membranes) are particularly sensitive to these effects of gaseous pollutants, which result in particular in accelerated aging of the skin, with a complexion which lacks radiance and an early formation of wrinkles or fine lines, and also in a decrease in the vitality and a dull appearance of the hair.

It is also known that the irradiation phenomena caused by exposure to ultraviolet rays also lead to the phenomena of accelerated cellular aging.

Whether they are of endogenous or exogenous origin, free radicals cause substantial oxidative damage, in particular in the cell membranes (peroxidation of lipids causing a deterioration of the permeability of membranes), the cell nuclei (destruction of DNA) and the tissues, in particular the connective tissue (degradation of the elastin and collagen fibers, depolymerization of the polyuronic fibers). This damage leads in particular to drying and a loss of firmness and of elasticity of the skin (Grinwald et al., 1980, Agren et al., 1997).

Specialists currently consider that one of the causes of cellular aging is the reduction in the defense capabilities against free radicals and against oxidation phenomena (in particular the formation of superoxide ions) which they initiate.

The superoxide ion $O^{°-}_2$ (active oxygen) is a radical ion whose instability and reactivity make it a toxic compound, because it generates, in particular in the presence of metal ions, highly harmful hydroxyl free radicals $(OH°)$. Superoxide dismutases (SOD) are enzymes which exert a protective effect in particular by trapping the superoxide ions and thus constitute a biological system of defence against the harmful effects of free radicals.

Superoxide dismutases are capable of inducing the dismutation of the superoxide ions, according to the reaction:

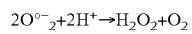

$$2 O^{°-}_2 + 2 H^+ \rightarrow H_2O_2 + O_2$$

Numerous superoxide dismutases are known. For example, superoxide dismutases extracted from bovine erythrocytes (Markovitz, J. Biol. Chem. 234, p. 40, 1959) and superoxide dismutases extracted from *Escherichia coli* (Keele and Fridovich, J. Biol. Chem., 245, p. 6176, 1970) have already been described. In the document FR-A-2,225, 443 are described superoxide dismutases extracted from marine bacterial strains, and their method of preparation.

Superoxide dismutases make it possible in particular to protect the skin and the hair, in particular by maintaining the integrity of the natural keratin structure, as describes for example the document FR-A-2,287,899. In addition, superoxide dismutases improve cutaneous cell respiration and maintain or improve the qualities of the skin, such as softness to the touch, suppleness and elasticity.

Superoxide dismutases also protect the skin against the inflammation phenomena caused by ultraviolet radiation and against accelerated skin aging, in particular under the influence of such radiation.

Because of these advantageous properties, it is known to add superoxide dismutases to cosmetic compositions, in particular compositions intended for topical application (see, for example, EP-0-673,643 and EP-0-636,360).

SUMMARY OF THE INVENTION

The Applicant has discovered a novel means of combating the harmful effects caused by free radicals by inducing the endogenous synthesis of superoxide dismutase. Indeed, it has discovered, most surprisingly, that an extract of a nonfruiting and nonphotosynthetic filamentous bacterium caused an increase in the endogenous synthesis of superoxide dismutase.

The topical use of substances with superoxide dismutase activity, while it can be advantageous under certain conditions of use, exhibits nevertheless the disadvantage of requiring particular stability and cutaneous bioavailability of these SOD forms. Moreover, it is known that a particular distribution of SODs exists in cells, in particular they are physiologically located inside the cells and more particularly in direct proximity with cellular entities which strongly generate superoxide ions, such as the mitochondria. Thus, when means are used for neutralizing the superoxide ions produced outside the cell, it is because the oxidative cellular damage is already very extensive and the superoxide anion has left the control of its intracellular environment. The use of exogenous SOD is therefore designed to prevent the propagation of oxidative damage to other cellular entities which can fulfil both a curative and repair function.

The Applicant presents here a means of inducing the cells to produce their own antioxidant activity and to thus strengthen their natural defenses. The advantage of the use according to the present invention compared with the use of an exogenous substance exhibiting an SOD activity is that it makes it possible, after contact between the cells and the membrane extract of nonfruiting nonphotosynthetic filamentous bacterium, to induce the production of the SOD enzyme according to a localization (in particular mitochondrial) which respects the physiological conditions and in particular induces the cell to protect itself from inside by virtue of its own oxidative metabolism. Furthermore, SOD, when it captures free radicals, itself undergoes oxidation and gradually loses its resistance to oxidative damage, this is even more manifest when the enzyme has left its intracellular context. The induction of SOD in response to the application of an extract of a nonfruiting nonphotosynthetic filamentous bacterium thus allows the cell to self-reconstruct and to accelerate the physiological renewal of its intracellular stock of SOD.

Increasing the endogenous synthesis of superoxide dismutases has numerous advantages compared with the exogenous supply of the enzyme. Indeed, during topical application of compositions containing SODs, a large proportion of SODs are denatured in particular by proteases present at the surface of the skin and/or not crosslinking the cell membranes because of their large molecular weight (17 kD for Cu/Zn-SOD and 23 kD for MnSOD). Accordingly, to obtain the desired effect, it is generally necessary to increase the quantity of SOD in the composition.

Another disadvantage of the topical application of an exogenous protein, such as the SOD enzyme, is the risk of allergy which it represents when the protein concentration is too high.

The subject of the present invention is therefore the cosmetic use of an extract of a nonfruiting nonphotosynthetic filamentous bacterium in a composition containing a cosmetically acceptable medium, as an agent increasing the endogenous synthesis of superoxide dismutase.

DETAILED DESCRIPTION OF BEST MODE AND SPECIFIC/PREFERRED EMBODIMENTS OF THE INVENTION

The bacterial extracts according to the invention are prepared from nonfruiting and nonphotosynthetic filamentous bacterium as defined according to the classification of Bergey's Manual of Systematic Bacteriology (Vol. 3, section 23, 9th Edition, 1989), among which there may be mentioned bacteria belonging to the order Beggiatoales, and more particularly bacteria belonging to the genera *Beggiatoa, Vitreoscilla, Flexithrix* or *Leucothrix*.

Various extracts may be used, in particular it is preferable to use, as an extract of a nonfruiting nonphotosynthetic filamentous bacterium, a lipopolysaccharide isolate which may, for example, be obtained according to one of the methods described in Example 1.

The preferred nonfruiting nonphotosynthetic filamentous bacterium according to the present invention is *Vitreoscilla filiformis*, in particular the strain ATCC 15551.

Human cells synthesize two types of superoxide dismutases, superoxide dismutase type 1, also called Cu/ZnSOD or SOD of the cytosol, is an enzyme which is found in the cytosol of cells. Superoxide dismutase type 2, MnSOD, is found in the mitochondria of the cells. The Applicant has observed, most surprisingly, that the extract of a nonfruiting nonphotosynthetic filamentous bacterium was particularly effective for increasing the synthesis of MnSOD by a transcriptional route involving an increase in the production of messenger RNA, a precursor for its protein synthesis.

Accordingly, a variant of the invention relates to the cosmetic use of an extract of a nonfruiting nonphotosynthetic filamentous bacterium in a composition containing a cosmetically acceptable medium, as an agent increasing the endogenous synthesis of superoxide dismutase type 2 (MnSOD).

In the compositions according to the invention, it is possible to use 0.001% to 10%, and in particular from 0.01% to 1%, by weight of dry extract of nonfruiting nonphotosynthetic filamentous bacterium relative to the weight of the composition.

In particular forms of applications of the balneotherapy type, it is also possible to envisage applications of native or reconstituted bacterial lysates in higher proportions which may be up to 100%.

These compositions may contain the *Vitreoscilla filiformis* extract in the form of a dispersion in an appropriate vehicle such as, for example, water, organic solvents, fatty substances including oils, and mixtures thereof, in particular emulsions.

According to another subject of the present invention and for all the applications described below, during the cosmetic use of the extract of a nonfruiting nonphotosynthetic filamentous bacterium in a composition containing a cosmetically acceptable medium, the extract of a nonfruiting nonphotosynthetic filamentous bacterium may be combined with an antioxidant.

Thus, it is possible, for example, to use an antioxidant chosen from:

vitamin E (tocopherol) and its derivatives, inter alia acetate, linoleate or nicotinate, preferably at concentrations of the order of 0.1% to 5%, γ-orizanol (0.1% to 5%), lysine or arginine pidolates (0.5% to 10%), plant extracts such as Melissa extract (0.01% to 2%), silimarin extract (0.01% to 2%), gingko biloba extract (0.05% to 2%), sage extract (0.05% to 2%), kola nut extract (0.05% to 2%), rutin extract (0.1% to 2%) or thyme extract (0.1% to 2%), the % being given as dry matter, lycopene in purified form or alternatively in an extract (for example tomato paste having a lycopene titre resulting in a final lycopene concentration of between $10^{-12}$% and 10%, and more preferably from $10^{-7}$% to 0.1%), pine, hawthorn or grape proanthocyanolidic oligomers (0.1% to 2%), di-tert-butyl-hydroxybenzylidenecamphor (0.1% to 2%), green tea (0.1% to 2%), caffeine (0.1% to 5%), glycerol (2% to 30%), mannitol (2% to 30%), carnosine (0.1% to 2%), superoxide dismutase (100 to 10 000 IU/100 g), guanosine (0.01% to 1%), microalgae containing ethoxyquin such as Hematococcus (0.005% to 1%), pentasodium aminotrimethylene phosphonate (0.001% to 0.5%), lactoperoxydase (0.01% to 0.1%), and lactoferrin (0.01% to 0.1%).

It is also possible to use a mixture of several antioxidants.

There may also be mentioned anti-free radical agents, in particular biflavonoids, coenzyme Q10 or ubiquinone; certain enzymes such as catalase, glutathione peroxidase and quinine reductases; glutathione; benzylidenecamphor; benzylcyclanones; substituted naphthalenones; pidolates; phytantriol; lignans; and melatonin.

Preferably, the antioxidant is lycopene.

In another embodiment according to the invention, the antioxidant is a superoxide dismutase. It will be possible, for example, to use the SOD enzyme extracted from bovine erythrocytes (Markovitz, J. Biol. Chem. 234, p. 40, 1959), from *Escherichia coli* (Keele and Fridovich, J. Biol. Chem., 245, p. 6176, 1970) or alternatively from marine bacterial strains (FR-A-2,225,443).

The present invention also relates to the cosmetic use of an extract of a nonfruiting nonphotosynthetic filamentous bacterium in a composition containing a cosmetically acceptable medium, for preventing and/or limiting the formation of free radicals and/or removing the free radicals present in cells.

Another subject to the invention relates to cosmetic use of an extract of a nonfruiting nonphotosynthetic filamentous bacterium in a composition containing a cosmetically acceptable medium, for preventing and/or combating the harmful effects of UV radiation and/or of pollution on the skin.

Clinically, the harmful effects of UV radiation and/or of pollution on the skin generally result in accelerated aging, that is to say in the appearance of wrinkles and fine lines, in a loosening of the cutaneous and subcutaneous tissues, in a loss of cutaneous elasticity and in skin texture atony. The loss of firmness and of tonicity of the skin, such as wrinkles and fine lines, is explained, at least in part, by dermal atrophy and flattening of the dermal/epidermal junction; the skin is less firm and more flaccid, and the thickness of the epidermis decreases.

In addition, the complexion of the skin is generally modified, it appears more pale and more yellow. This phenomenon appears to be essentially due to disorganization of the microcirculation (less haemoglobin in the papillary dermis). Another clinical sign of aging is the dry and rough appearance of the skin which is essentially due to greater desquamation; these squamas, by diffracting the light rays, also participate in the slightly grey appearance of the complexion. Furthermore, numerous colored and/or dark spots appear at the surface of the skin, and more especially on the hands, conferring heterogeneity on the skin. In general, these spots are due to the high production of melanin in the epidermis and/or the dermis of the skin. Moreover, diffuse irritations and sometimes telagiectasias may exist on certain areas of the skin. Some of these signs are more particularly linked to intrinsic or physiological aging, that is to say aging linked to age, whereas others are more specific to extrinsic aging, that is to say aging caused in general by the environment; it is more particularly photoaging due to exposure to the sun, light or any other radiation.

Accordingly, the subject of the invention is more particularly suited to the cosmetic use of an extract of a nonfruiting nonphotosynthetic filamentous bacterium in a composition containing a cosmetically acceptable medium, for preventing and/or treating the loss of firmness and/or elasticity of the skin. Such a use allows in particular the skin to rediscover a uniformly smooth appearance.

Another subject of the invention is the cosmetic use of an extract of a nonfruiting nonphotosynthetic filamentous bacterium in a composition containing a cosmetically acceptable medium, for preventing and/or treating dull complexion.

The invention is also suited to the cosmetic use of an extract of a nonfruiting nonphotosynthetic filamentous bacterium in a composition containing a cosmetically acceptable medium, for preventing and/or treating skin dehydration.

More generally, the subject of the invention is also suited to the cosmetic use of an extract of a nonfruiting nonphotosynthetic filamentous bacterium in a composition containing a cosmetically acceptable medium, for preventing and/or treating the signs of skin aging.

The expression signs of skin aging is understood more particularly to mean pigmented spots and/or hyperkeratosis spots and/or epidermal atrophy and/or skin roughness and/or skin dryness.

As explained above, an undesirable effect of the presence of free radicals in the skin is that they cause a phenomenon of peroxidation of lipids. With age (more particularly from forty years), the accumulation of these peroxidized lipids is responsible for bad body odors such as a rancid odor (Haze S. et. al. J. Invest. Dermatol. 2001, 116(4): 520-4).

The subject of the invention is suited to the cosmetic use of an extract of a nonfruiting nonphotosynthetic filamentous bacterium in a composition containing a cosmetically acceptable medium, for preventing and/or limiting and/or eliminating the peroxidation of skin lipids.

Accordingly, the subject of the invention is also useful for preventing and/or limiting and/or eliminating bad body odours.

In the particular case of exposure of the skin to the sun, it appears that moderate exposure to UVA and UVB induces, in the first instance, a reduction in skin SODs (Leccia et al., Exp. Dermatol. 2001, 10(4): 272-9). Five days after this exposure, a rebound effect is observed with an increase in the activity of the SODs. Thus, a transitional period is necessary for putting in place a skin antioxidant protective system.

By virtue of its capacity to increase the endogenous synthesis of SOD, the extract of a nonfruiting nonphotosynthetic filamentous bacterium makes it possible to accelerate the putting in place of the skin antioxidant protective system and to prepare the skin for solar exposure.

Accordingly, the cosmetic use according to the invention of an extract of a nonfruiting nonphotosynthetic filamentous bacterium in a composition containing a cosmetically acceptable medium is particularly well suited for preparing the skin for solar exposure.

In particular, the preparation of the skin for solar exposure may be carried out by daily application, to the skin, of the said cosmetic composition for one week before the solar exposure and, preferably, for two weeks, up to at least one night (between 6 and 18 hours) before the solar exposure.

The use according to the present invention is also useful during and after solar exposure for maintaining a high level of SOD synthesis and to attenuate and/or repair the damage linked to solar exposure such as redness, skin irritations and sensations of overheating of the skin.

The subject of the invention may also consist in the cosmetic use of an extract of a nonfruiting nonphotosynthetic filamentous bacterium in a composition containing a cosmetically acceptable medium for attenuating and/or repairing the redness and/or the skin irritations and/or the sensations of overheating of the skin caused by solar exposure.

Preferably, the cosmetic composition used according to the present invention is suited to topical application.

The use of an extract of a nonfruiting nonphotosynthetic filamentous bacterium in a cosmetic composition according to the invention may also be provided in the form of a hair tonic for revitalizing the scalp and for improving the appearance of the hair.

In another variant of the invention, the use of an extract of a nonfruiting nonphotosynthetic filamentous bacterium in a cosmetic composition is applied to the nails in order to revitalize the nails. In such an application, the cosmetic composition may for example be provided in the form of a varnish or a gel or a cream for massaging the nails.

Another subject of the present invention relates to the use of at least one extract of a nonfruiting nonphotosynthetic filamentous bacterium for the preparation of a pharmaceutical or dermatological composition intended for increasing the endogenous synthesis of superoxide dismutase.

Thus, the use of at least one extract of a nonfruiting nonphotosynthetic filamentous bacterium may also be useful for the preparation of a dermatological composition intended for preventing and/or limiting the formation of free radicals and/or for eliminating the free radicals present in cells.

In particular, the present invention relates to the use of at least one extract of a nonfruiting nonphotosynthetic filamentous bacterium for the preparation of a dermatological composition intended for repairing the damage caused by solar exposure, in particular when the damage caused by solar exposure is a skin erythema or a skin oedema.

The present invention also relates to the use of at least one extract of a nonfruiting nonphotosynthetic filamentous bacterium for the preparation of a dermatological composition intended for preventing and/or limiting and/or eliminating the oxidation phenomena caused by the colonization of the skin by microorganisms. Preferably, the invention relates to the use of at least one extract of a nonfruiting nonphotosynthetic filamentous bacterium for the preparation of a dermatological composition intended for treating acne.

It has been shown that the tissues of a psoriatic skin highly expressed mRNAs encoding MnSOD and that this phenomenon represented a response designed to protect the cells (Lontz et al., Free Radic. Biol. Med. 1995; 18(2): 349-55). By increasing the endogenous synthesis of MnSOD, the use according to the invention contributes to the treatment of psoriatic skins. Accordingly, the subject of the invention is suited to the use of at least one extract of a nonfruiting nonphotosynthetic filamentous bacterium for the preparation of a dermatological composition intended for treating psoriasis.

Moreover, a study on a model of carcinogenesis of the skin comparing the progression of tumours in transgenic mice expressing MnSOD in the skin and in wild-type mice has shown that the expression of MnSOD had as a consequence the inhibition of the development of tumours (Zhao et al., Cancer Res. 2001, 61(16): 6082-8). Accordingly, the subject of the invention is suited to the use of at least one extract of a nonfruiting nonphotosynthetic filamentous bacterium for the preparation of a dermatological composition intended for inhibiting the development of cancerous skin tumours.

The present invention also relates to the use of at least one extract of a nonfruiting nonphotosynthetic filamentous bacterium for the preparation of a dermatological composition intended for preventing and/or treating the signs of epidermal aging. These signs of skin aging are in particular pigmented spots and/or hyperkeratosis spots and/or epidermal atrophy and/or skin roughness and/or skin dryness.

In another variant, the present invention relates to a composition containing, in a physiologically acceptable medium at least one extract of a nonfruiting nonphotosynthetic filamentous bacterium, preferably an extract of *Vitreoscilla filiformis*, and lycopene.

Lycopene is a natural pigment which is found in ripe fruits, particularly in tomatoes. It belongs to the family of carotenoids and its structure is close to that of β-carotene.

The role of lycopene in the maturation of fruits is known in the prior art.

Lycopene is used in compositions with tanning activity for its role on the synthesis of melanin (WO 97/47278), in compositions intended for the treatment of hair and/or of acne for its activity on 5α-reductases (JP-2940964) or alternatively as anti-free radical agent (JP-A-8-283136).

Lycopene is also described as an inhibitor of the expression of proteases of the extracellular matrix, particularly metalloproteinases, such as for example collagenases (EP-A-1,090,628).

Lycopene may be in the cis or trans chemical form.

To give an order of magnitude, pure lycopene may be used in a quantity representing from $10^{-9}\%$ to $0.1\%$ of the total weight of the composition, and preferably in a quantity representing from $10^{-7}\%$ to $10^{-3}\%$ of the total weight of the composition.

To give another order of magnitude, some tomato pastes sold on the market, such as Lyc-O-Derm® (Lycored) have a pure lycopene titre of 10%; it is therefore possible to use a quantity of pasty tomato extract in proportions ranging from $10^{-6}\%$ to $10^{-2}\%$ of tomato extract.

In the particular applications of balneotherapy, it is possible to envisage contact with the skin in proportions where the tomato extract may be applied pure and may reach lycopene titres applied to the skin or the mucous membranes which may range from 1% to 15%.

The subject of the present invention is also a composition containing, in a physiologically acceptable medium, at least one extract of *Vitreoscilla filiformis* and a compound having a catalase activity.

As compounds which have a catalase activity, it is possible to use in particular catalases of natural (plant or animal) origin or catalases which have been modified chemically or by grafting, by adsorption onto supports, or by encapsulation (see in particular Patent Applications FR-2-716,884 and GB-793,739).

It is also possible to use commercial catalases such as Catalase NL® which are sold by the company Amano Enzyme Europe Ltd.

The subject of the present invention may also be a composition containing, in a physiologically acceptable medium, at least one extract of *Vitreoscilla filiformis* and a compound having a peroxidase activity.

As compounds having a peroxidase activity, it is possible to use in particular peroxidases of natural (plant or animal) origin, or alternatively peroxidases which have been modified chemically or by grafting, by adsorption onto supports, or by encapsulation (see for example WO 01/46431 and WO 87/07838 and EP-A-0,397,227).

It is possible to use in particular lactoperoxidases, microperoxidases from fungi, myeloperoxidase, and the like. It is known that lactoperoxidase (abbreviated: LPO) is an enzyme which is found in particular in numerous mammalian tissues and secretions, which uses one of the numerous cellular electron donors to reduce organic peroxides of the ROOH type (R being an organic group). Lactoperoxidase is a commercial product sold in particular by the companies Sigma and Sederma.

It may also be possible to use recombinant peroxidases, for example recombinant LPO (WO 91/06639).

Finally, the composition according to the invention may contain, in a physiologically acceptable medium, at least one extract of *Vitreoscilla filiformis*, a compound having a catalase activity and a compound having a peroxidase activity.

The invention also relates to a method for the cosmetic treatment of the loss of firmness and/or of elasticity of the skin, comprising the application, to the skin, of a composition containing, in a cosmetically acceptable medium, at least one extract of *Vitreoscilla filiformis*.

The invention relates to a method of cosmetic treatment for preparing the skin for solar exposure, comprising the application to the skin of a composition containing, in a cosmetically acceptable medium, at least one extract of *Vitreoscilla filiformis*.

The compositions used according to the invention may be provided in all the forms which may be envisaged in the cosmetic and pharmaceutical, in particular dermatological, field.

The composition according to the invention is preferably suited to topical application to the skin. It may be provided in all the galenic forms normally used for this type of application, in particular in the form of an aqueous or oily solution, an oil-in-water or water-in-oil or multiple emulsion, a silicone emulsion, a macroemulsion or nanoemulsion, an aqueous or oily gel or a liquid, pasty or solid anhydrous product.

This composition may be more or less fluid and may have the appearance of a white or coloured cream, an ointment, a milk, a lotion, a serum, a paste, a mousse or a gel. It may optionally be applied to the skin in the form of an aerosol. It may also be provided in solid form, for example in the form of a stick. It may be used as a care product and/or as a make-up product for the skin.

It may even be, in applications in the same category as balneotherapy, a crude extract.

To reinforce the anti-aging effects of the composition according to the invention, it may contain, in addition to the extract of a nonfruiting nonphotosynthetic filamentous bacterium described above, at least one compound chosen from: desquamating and/or moisturizing agents; depigmenting or propigmenting agents; antiglycation agents; agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents; agents acting on the microcirculation; agents acting on the energy metabolism of the cells; tightening agents; and mixtures thereof.

Thus, the composition according to the invention may in particular contain at least one active agent chosen from: α-hydroxy acids; salicyclic acid and its derivatives such as 5-(n-octanoyl)salicyclic acid; HEPES; procysteine; O-octanoyl-6-D-maltose; the disodium salt of methylglycinediacetic acid; ceramides; steroids such as diosgenin and derivatives of DHEA; kojic acid; N-ethyloxycarbonyl-4-para-aminophenol; ascorbic acid and its derivatives; bilberry extracts; retinoids and in particular retinol and its esters; polypeptides and their acylated derivatives; phytohormones; extracts of the yeast *Saccharomyces cerevisiae*; extracts of algae; extracts of soyabean, lupin, maize and/or pea; alverine and its salts, in particular alverine citrate; resveratrol; carotenoids and in particular lycopene; tocopherol and its esters; coenzyme Q10 or ubiquinone; xanthines and in particular caffeine and natural extracts containing it; extracts of butcher's broom and of horse chestnut; and mixtures thereof, without this list being limiting.

The composition according to the invention may in addition contain at least one UVA and/or UVB sun screening agent. The sunscreens may be chosen from organic screening agents, inorganic screening agents and mixtures thereof.

As examples of organic screening agents which are active in UV-A and/or UV-B, there may be mentioned in particular those designated below by their CTFA name:

para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONA/EM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, β,β,-diphenylacrylate derivatives: Octocrylene sold in particular under the trademark "UVINUL N539" by BASF, Etocrylene, sold in particular under the trademark "UVINUL N35" by BASF, benzophenone derivatives: Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof.

The organic UV-screening agents which are more particularly preferred are chosen from the following compounds:

Ethylhexyl Salicylate,
Butyl Methoxydibenzoylmethane,
Ethylhexyl Methoxycinnamate,
Octocrylene,
Phenylbenzimidazole Sulphonic Acid,
Terephthalylidene Dicamphor Sulphonic,
Benzophenone-3,
Benzophenone-4,
Benzophenone-5,
4-Methylbenzylidene camphor,
Benzimidazilate,
Anisotriazine,
Ethylhexyl triazone,
Diethylhexyl Butamido Triazone,
Methylene bis-Benzotriazolyl Tetramethylbutylphenol,
Drometrizole Trisiloxane,
and mixtures thereof.

The inorganic screening agents which may be used in the composition according to the invention are in particular nanopigments (mean size of the primary particles: generally between 5 nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides. Coating agents are moreover alumina and/or aluminum stearate. Such nanopigments of metal oxides, coated or uncoated, are in particular described in EP-A-0-518,772 and EP-A-0-518,773.

In a known manner, the composition of the invention may also contain the customary adjuvants in the cosmetic and dermatological fields, such as hydrophilic or lipophilic gelling agents, preservatives, antioxidants, solvents, perfumes, fillers, pigments, odour absorbers and colouring matters. The quantities of these various adjuvants are those conventionally used in the fields considered, and for example from 0.01% to 20% of the total weight of the composition. These adjuvants, depending on their nature, may be introduced into the fatty phase or into the aqueous phase. These adjuvants, and their concentrations, should be such that they do not damage the advantageous properties of the extract of the nonfruiting non-photosynthetic filamentous bacterium.

As oils which may be used in the composition of the invention, there may be mentioned for example:

hydrocarbon oils of animal origin, such as perhydrosqualene;

hydrocarbon oils of plant origin, such as the liquid triglycerides of fatty acids containing from 4 to 10 carbon atoms and the liquid fraction of shea butter;

esters and synthetic esters, in particular of fatty acids, such as the oils of formulae $R^1COOR^2$ and $R^1OR^2$ in which $R^1$ represents the residue of a fatty acid containing from 8 to 29 carbon atoms, and $R^2$ represents a hydrocarbon chain, branched or unbranched, containing from 3 to 30 carbon atoms, such as for example Purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octylhydroxystearate, octyldodecyl hydroxystearate, diisostearyl malate, triisocetyl citrate, heptanoates, octanoates, decanoates of fatty alcohols; polyol esters, such as propylene glycol dioctanoate, neopentylglycol diheptanoate and diethylene glycol diisononanoate; and pentaerythritol esters such as pentaerythrityl tetraisostearate;

linear or branched hydrocarbons, of inorganic or synthetic origin such as volatile or non-volatile paraffin oils and derivatives thereof, petroleum jelly, polydecenes, hydrogenated polyisobutene such as parleam oil;

fatty alcohols having from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol and linoleyl alcohol;

partially hydrocarbon-based and/or silicone-based fluorinated oils such as those described in the document JP-A-2-295912;

silicone oils such as volatile or non-volatile polymethylsiloxanes (PDMS) containing a linear or cyclic silicone which are liquid or pasty at room temperature, in particular cyclopolydimethylsiloxanes (cyclomethicones) such as cyclohexasiloxane; polydimethylsiloxanes containing alkyl, alkoxy or phenyl groups, which are pendant or at the silicone chain end, groups having from 2 to 24 carbon atoms; phenylated silicones such as phenyltrimethicones, phenyldimethicones, phenyltrimethylsiloxydiphenylsiloxanes, diphenyldimethicones, diphenylmethyldiphenyltrisiloxanes, (2-phenylethyl) trimethylsiloxysilicates, and polymethylphenylsiloxanes;

mixtures thereof.

As emulsifiers and coemulsifiers which can be used in the invention, there may be mentioned, for example, O/W emulsifiers such as esters of a fatty acid and polyethylene glycol, in particular PEG-100 stearate, and esters of the fatty acid and glycerine such as glyceryl stearate, and W/O emulsifiers such as oxyethylenated poly(methylcetyl)(dimethyl)methylsiloxane available under the trademark ABIL WE09 from the company Degussa Goldschmidt or the mixture of ethylene glycol acetyl stearate and glyceryl tristearate marketed by the company Guardian under the trademark UNITWIX.

As hydrophilic gelling agents, there may be mentioned in particular carboxyvinyl polymers (carbomer), acrylic copolymers such as acrylate/alkyl acrylate copolymers, polyacrylamides, polysaccharides, natural gums and clays, and, as lipophilic gelling agents, there may be mentioned modified clays such as bentones, metal salts of fatty acids, hydrophobic silica and polyethylenes.

As fillers which may be used in the composition of the invention, there may be mentioned, for example, in addition to pigments, silica powder; talc; starch crosslinked with octenylsuccinic anhydride marketed by the company National Starch under the name DRY FLO PLUS (28-1160); polyamide particles and in particular those sold under the name ORGASOL by the company Atochem; polyethylene powders; microspheres based on acrylic copolymers, such as those in the form of an ethylene glycol dimethacrylate/lauryl methacrylate copolymer sold by the company Dow Corning under the name POLYTRAP; expanded powders such as hollow microspheres in particular the microspheres marketed under the name EXPANCEL by the company Kemanord Plast or under the name MICROPEARL F 80 ED by the company Matsumoto; microbeads of silicone resin such as those marketed under the name TOSPEARL by the company Toshiba Silicone; and mixtures thereof. These fillers may be present in quantities ranging from 0% to 20% by weight and preferably from 1% to 10% by weight relative to the total weight of the composition or of the preparation according to the invention.

In order to further illustrate the present invention and the advantages thereof, the following specific examples are given, it being understood that same are intended only as illustrative and in nowise limitative.

EXAMPLES

Example 1

Preparation of an Extract of *Vitreoscilla filiformis* Containing Lipopolysaccharides (M. A. Apicella, J. McLeod Gritliss, and H. Schneider, 1994 Methods in enzymology, Vol. 235, (242-252))

Various methods make it possible to isolate the fraction of interest containing the lipopolysaccharides:
- the modified phenol-water method (Johnson and Perry, 1975, Can J. Microbial, 22, p 29) described in paragraph 1;
- the Darveau and Hancock method (1983, J. Bact. 155, p 831) which uses SDS to solubilize the lipopolysaccharides, which makes it possible to separate them from the insoluble peptidoglycan, this method is described in paragraph 2. The proteins are removed from the fraction containing the lipopolysaccharides by enzymatic digestion (Pronase), the lipopolysaccharide fraction is then precipitated with ethanol.
- the method of extraction using proteinase K described in paragraph 3.

1. Modified Phenol Technique:

1.1. Preparation of the Crude Lipopolysaccharides:

25 ml of 50 mM Na phosphate buffer, pH 7, containing 5 mM EDTA, are added to 5 g of *Vitreoscilla filiformis* bacteria (ATCC 15551) frozen or dried with acetone in powdered form, and the mixture is stirred.

The following steps are then carried out:
- adding 100 mg of lysozyme, stirring overnight at 4° C. and then incubating at 37° C. for 20 min;
- centrifuging for 3 min at low speed,
- adjusting the volume to 100 ml with 50 mM Na phosphate buffer pH 7 containing 20 mM $MgCl_2$;
- adding Rnase, Dnase (at 1 µg/ml), incubating for 60 min at 37° C. and then for 60 min at 60° C.;
- the bacterial suspension is placed on a bath at 70° C., and an equal volume of 90% phenol (w/v), preheated to 70° C., is added thereto,
- it is cooled by stirring for 15 min on an ice bath,
- centrifuging at 18,000 g for 15 min at 4° C.

A marked interface is produced between the aqueous and phenolic phases. The aqueous phase contains the lipopolysaccharides; after dialyzing against water, this phase is freeze-dried.

1.2. Purification of the Crude Lipopolysaccharides 20 to 35 mg of the lipopolysaccharides/ml of distilled water are centrifuged at low speed (1100 g, 5 min). The supernatant obtained is then centrifuged at high speed (105,000 g, 16 h, 4° C.). The pellet is suspended in water, the centrifugation is repeated until purified lipopolysaccharides are obtained. The final pellet is resuspended in water and freeze-dried.

2. SDS Method:

15 ml of 10 mM Tris-HCl buffer pH 8 containing 2 mM $MgCl_2$, 100 µg/ml Dnase and 25 µg/ml Rnase are added to 500 mg of dried *Vitreoscilla filiformis* bacterial cells (ATCC 15551). The mixture is subjected to a French press twice, 15,000 psi, and then sonication, twice at 6 W, 30 sec.

The following steps are then applied:
- adding Dnase 200 µg final and Rnase 50 µg final, incubating 37° C. 2 h,
- adding 5 ml 0.5 M EDTA in 10 mM Tris-HCl pH 8, 2.5 ml 20% SDS dissolved in 10 mM Tris-HCl and 2.5 10 mM Tris-HCl pH 8.

The final volume obtained is 25 ml containing 0.1 M EDTA; 2% SDS and 10 mM Tris-HCl pH 9.5, the mixture is vortexed and centrifuged at 50,000 g for 30 min at 20° C.

The supernatant is separated after settling out. The sediment which contains the peptidoglycan is discarded. Pronase is added to the supernatant at a final concentration of 200 µM, incubation follows at 37° C. overnight, with stirring (if a precipitate forms, remove it by centrifuging at 1000 g 10 min).

The lipopolysaccharides are precipitated with 95% ethanol (v/v) containing 0.376 M $MgCl_2$–70° C., and then centrifuged (12,000 g, 15 min, 4° C.).

The pellet obtained is suspended in 25 ml 2% SDS, 0.1 M EDTA, 10 mM Tris-HCl pH 8, sonicated and then incubated at 85° C., 10 to 30 min. After cooling, the solution is adjusted to pH 9.5.

Pronase is added at 25 µg/ml, incubation at 37° C., overnight, with stirring.

The lipopolysaccharides are again precipitated with ethanol 95% (v/v) containing 0.376 M $MgCl_2$, and then centrifuged (12,000 g 15 min 4° C.). To remove the insoluble $Mg^{2+}$-EDTA crystals, the pellet is resuspended in 15 ml of 10 mM Tris-HCl buffer pH 8, sonicated and centrifuged (1000 g, 5 min). The supernatant is then centrifuged (200,000 g, 2h 15° C.) in the presence of 25 mM $MgCl_2$. The pellet which contains the lipopolysaccharides is suspended in distilled water.

3. Extraction of the Lipopolysaccharides Using Proteinase K (Zanen and, 1988, FEMS Microbiology Letters 50, 85-88):

30 ml of buffer containing 2% SDS, 5% 2-mercaptoethanol, 10% glycerol and 0.25 M Tris-HCl pH 6.8 are added to 1.5 g of freeze-dried *Vitreoscilla filiformis* cells (ATCC 15551).

The mixture is incubated for 15 to 30 min, 100° C., centrifuged (10,000 g, 30 min, 4° C.). The supernatant (20 ml) is recovered, 12 mg of proteinase K are added, the medium is incubated at 60° C. for 1 h and the lipopolysaccharides are precipitated with 95% ethanol (v/v) containing 0.376 M $MgCl_2$, –20° C. overnight, reprecipitating the lipopolysaccharides with 95% ethanol (v/v) under the same conditions as above, the pellet obtained is suspended in 10 ml of water, dialysed and then freeze-dried.

Example 2

Formulations

Composition 1—Regenerating Cream:

| | |
|---|---|
| Extract of Example 1 (freeze-dried extract obtained according to method 3) | 0.1% |
| Carbomer 940 ® (cross-linked polyacrylic acid) | 0.3% |
| Triethanolamine | 0.3% |
| Stearic acid | 3.0% |
| Cetyl alcohol | 2.0% |
| Self-emulsifiable glyceryl monostearate | 3.0% |
| Soyabean oil | 10.0% |
| Lanolin alcohol | 2.0% |
| Isopropyl myristate | 4.0% |
| Cetyl stearyl 2-ethylhexanoate | 4.0% |
| Perhydrosqualene | 3.0% |
| Paraffin | 2.0% |
| Glycerine | 3.0% |
| Preservatives | 0.3% |
| Water | qs 100% |

To prepare this cream, the aqueous phase containing the glycerine, the preservatives and the water is heated to 80° C.;

the Carbomer 940 is dispersed therein and then neutralized with dry ethanolamine. The fatty phase, heated, and homogenized, to 80° C., is introduced, with vigorous stirring, into the aqueous phase. The extract of the example is dispersed in 10 g of water and introduced at 40° C. into the cream, with stirring. The whole is cooled to room temperature. This cream is applied to the skin of the face and of the neck once or twice by day. It makes it possible in particular, after using for a few days, to increase the regeneration of the epidermis and to give a younger appearance to the skin.

Composition 2—Care Gel for the Face:

| | |
|---|---|
| Extract of Example 1 (freeze-dried extract obtained according to method 3) | 0.05% |
| Hydroxypropylcellulose (Klucel H sold by the company Hercules) | 1.00% |
| Antioxidant | 0.05% |
| Isopropanol | 40.00% |
| Preservative | 0.30% |
| Water | qs 100% |

This gel is obtained by mixing the constituents in water and adding the gelling agent last.

As for Composition 1, it may be applied twice by day; it is particularly suitable for application in the morning because it does not leave the skin greasy.

Composition 3—Regenerating Cream:

| | |
|---|---|
| Extract of Example 1 (freeze-dried extract obtained according to method 3) | 1.0% |
| Preservatives | 0.85% |
| Alcohol | 5.0% |
| Tocopheryl acetate | 1.0% |
| Disodium EDTA | 0.05% |
| PEG-20 methyl glucose sesquistearate | 2.0% |
| Glycerine | 7.0% |
| Acrylate polymer | 0.25% |
| Cholesterol | 0.1% |
| Cyclohexasiloxane | 3.5% |
| Squalane | 9.5% |
| Water and extract of *Fagus sylvatica* | 2.0% |
| Ceramide | 0.05% |
| Ammonium polyacryloyldimethyl taurate | 2.2% |
| Hydrolysed lupin protein | 1.0% |
| Vegetable oils | 6.0% |
| Polycaprolactone and *Solanum lycopersicum* (tomato) extract (lycopene) | 1.0% |
| Divinyldimethicone/dimethicone copolymer (and) C12-13 pareth-3 (and) C12-13 pareth-23 | 2.0% |
| Water | qs 100% |

This cream is preferably intended to be applied daily in the evening after cleansing the skin. This cream rapidly allows the skin to be better moisturized and to be softer; it makes the complexion bright and uniform and has a tightening effect which softens wrinkles and fine lines and smoothens the skin.

Composition 4—Regenerating Day Fluid:

| | |
|---|---|
| Extract of Example 1 (freeze-dried extract obtained according to method 3) | 1.0% |
| Octyldodecanol | 0.1% |
| Preservatives | 0.75% |
| Tocopheryl acetate | 1.0% |
| PEG-20 methyl glucose sesquistearate | 3.0% |
| Sodium hyaluronate | 0.1% |
| Glycerine | 7.0% |
| Cyclohexasiloxane | 9.5% |

-continued

| | |
|---|---|
| Water and extract of *Fagus sylvatica* | 1.0% |
| Ammonium polyacryloyldimethyl taurate | 1.0% |
| Cyclopentasiloxane (and) dimethicone | 7.5% |
| Hydrolysed lupin protein | 1.0% |
| Polycaprolactone and *Solanum lycopersicum* (tomato) extract (lycopene) | 1.0% |
| Vegetable oils | 3.0% |
| Divinyldimethicone/dimethicone copolymer (and) C12-13 pareth-3 (and) C12-13 pareth-23 | 2.0% |
| Water | qs 100% |

This fluid may be applied daily in the morning and in the evening. As for the preceding cream, this fluid improves the visual appearance of the skin and of the complexion by virtue of better moisturizing and a tightening effect.

Composition 5—Care Cream for Solar Erythema (oil-in-water Emulsion):

| | |
|---|---|
| Extract of Example 1 (freeze-dried extract obtained according to method 3) | 0.75% |
| Glyceryl stearate | 2.00% |
| Polysorbate 60 (Tween 60 sold by the company ICI) | 1.00% |
| Stearic acid | 1.40% |
| Glycyrrhetinic acid | 2.00% |
| Triethanolamine | 0.70% |
| Carbomer | 0.40% |
| Liquid fraction of shea butter | 12.00% |
| Sunflower oil | 10.00% |
| Lycopene | 0.05% |
| Perfume | 0.50% |
| Preservative | 0.30% |
| Water | qs 100% |

This cream should be applied twice by day for at least two days, and then once by day until the erythema completely disappears. By virtue of such an application, the skin more rapidly rediscovers its normal appearance.

Composition 6—Sunscreen:

| | |
|---|---|
| Extract of Example 1 (freeze-dried extract obtained according to method 3) | 3.5% |
| Mixture of cetylstearyl alcohol and oxyethylenated cetylstearyl alcohol (33 EO) 80/20 | 7.0% |
| Mixture of glyceryl mono- and distearate | 2.0% |
| Cetyl alcohol | 1.5% |
| Polydimethylsiloxane | 1.5% |
| Liquid paraffin | 15.0% |
| Butyl methoxydibenzoylmethane | 3.0% |
| Octocrylene | 7.0% |
| Glycerine | 20.0% |
| Demineralized water | qs 100% |

The application of this cream should precede exposure to the sun and should be repeated every two hours. Such an application prevents the damage which may be caused by the sun and accelerates the repair of this possible damage.

Composition 7—Composition for Preparing the Skin for the Sun:

| | |
|---|---|
| (The ingredients are indicated under their CTFA names) | |
| Extract of Example 1 (freeze-dried extract obtained according to method 3) | 0.5% |
| Preservatives | 1.35% |
| Sodium citrate | 0.035% |

-continued (The ingredients are indicated under their CTFA names)

| | |
|---|---|
| PEG-40 | 1.25% |
| Pentaerythrityl tetraethylhexanoate | 4% |
| Glycerine | 7% |
| Sorbitan tristearate | 0.3% |
| *Prunus Armeniaca* (apricot) Kernel oil | 2% |
| Cetyl alcohol | 0.7% |
| Propylene glycol | 2% |
| Triethanolamine | 0.4% |
| Cyclohexasiloxane | 2% |
| Carbomer | 0.75% |
| Tocopherol | 1% |
| Silica | 2% |
| Ascorbyl glucoside | 0.1% |
| Water - titanium dioxide - silica - alumina | 3% |
| Polycaprolactone - betacarotene | 5% |
| Water | qs 100% |

Daily application of this composition at least one week before solar exposure reduces the risks of erythema, burning and oedema (in particular if the skin is protected with Composition 4 during solar exposure) and makes if possible to obtain a tanning of better quality and longer lasting.

Example 3

Measurement of the Increase in the Synthesis of MnSOD

I. Materials and Methods:

Cell Cultures and Treatment:

The studies are carried out on normal human fibroblasts and on normal human epidermal keratinocytes in culture.

The dermal fibroblasts are cultured in DMEM medium (Life Technology, ref. 21969035) containing L-glutamine (2 mM, Life Technology, ref. 25030024), penicillin at 50 IU/ml and streptomycin at 50 μg/ml (Life Technology, ref. 15070063) and foetal calf serum at 1% (v/v, Life Technology, ref. 10106151).

The keratinocytes are cultured in SFM medium with no pituitary extracts and EGF.

The extract of *Vitreoscilla filiformis* obtained by applying method 3 of Example 1 was applied to the cells at the concentration of 0.1% (W/V). The contact time was 24 or 48 hours.

CDNA Array:

The methodology used is that recommended by Clontech (Palo Alto, USA). The extraction/purification of total RNA of each culture led to the isolation of quantities of total RNA of the order of 100 to 150 μg. The solutions of total RNA are treated with DNAse I in order to remove any trace of contaminating DNA, according to the supplier's recommendations. The quality of the RNA was then checked on agarose gel and the RNA solutions were adjusted to 1 μg/ml.

The next step was the purification of the messenger RNAs (mRNAs) by hybridization of the poly(A) ends of the mRNAs with biotinylated and capture-selective oligo(dT) primers on streptavidin beads, according to the Atlaspure (Clontech) protocol. The $^{33}$P-labelled DNA probes were prepared by reverse transcription of the mRNAs attached to poly(dT) beads, with the aid of a pool of primers specific for the sequences immobilized on the "arrays", in the presence of ($\alpha^{33}$P)-dATP. This step used the reagents and the protocol recommended by Clontech. The labelled probes were purified by chromatography on an exclusion column and the quality and the equivalence of the labelled probes was evaluated by liquid scintillation counting.

cDNA array membranes containing 1176 genes were pretreated and then the cDNAs immobilized on each membrane were hybridized (68° C., overnight) with the corresponding labelled probes. The filters were then extensively washed and placed in individual plastic bags for analysis. The analysis was carried out by direct quantification of the radioactivity of the spots with the aid of a Cyclone phosphoimager (Packard). The results are expressed in relative expression units (RE, radioactivity of the spot corresponding to each gene, corrected for the background noise and the differences in intensity of labelling of the probes).

RT-Q-PCR:

The pairs of primer used in this study are Mn+superoxide dismutase 2 precursor (size of the amplified fragment: 259 bp) and cytosolic superoxide dismutase 1 (size of the amplified fragment: 298 bp).

The total RNAs are extracted with the aid of Tri-Reagent according to the protocol recommended by the supplier. It is followed by another extraction with chloroform and precipitation with isopropanol. Potentially contaminating traces of DNA are removed by treating with the DNA-free system (Ambion). The reverse transcriptase reaction is then carried out in the presence of oligo(dT) primer and the enzyme Superscript II (Gibco). Each step is followed by quantification, by fluorescence, of the cDNA synthesized and adjustment of the concentrations to 150 ng/ml. Another quantification of each cDNA, after final dilution, is carried out before the PCR reaction.

The PCR reactions (polymerase chain reactions) were carried out by quantitative PCR with the "Light Cycler" system (Roche Molecular Systems Inc.) and according to the procedures recommended by the supplier. The reaction mixture (10 μl final) introduced into the capillaries of a thermocycler is composed of 2.5 μl of cDNA, primers for the two markers, reaction mixture (Roche) containing the enzyme Taq DNA polymerase, the marker SYBR Grenn I. The PCR conditions are the following: activation 10 min at 95° C., PCR reactions in 40 cycles, annealing 5 sec at 95° C. and then 5 sec at 60° C.

The analysis of fluorescence in the amplified DNA is measured continuously during the PCR cycles. The mean value of the relative expression (RE) is expressed as Arbitrary Units (AU) calculated from the values of cycles of two independent PCRs according to the following formula: $(\frac{1}{2}^{number\ of\ cycles}) \times 10^6$.

The results of expression of SOD are compared with that of actin in order to take into account possible differences in cell concentration in both cellular populations.

Flow Cytometry Study:

The cells are precultured at high density for 48 hours and then treated or otherwise with the test product for 24 or 48 hours. The cells are trypsinized and then rinsed with a PBS/2% FCS solution. The cells are transferred to Eppendorf tubes and centrifuged for 5' at 1500 rpm. The cells are fixed with a PBS-formalin solution at 4% final, 30' at room temperature and in the dark. They are then permeabilized with the aid of a 0.1% Triton-X100/0.1% citrate solution. The cells are labelled in the presence of anti-MnSOD (TEBU SOD-110) and anti-Cu/Zn SOD (TEBU SOD-100) antibodies according to the supplier's instructions. Secondary labelling is carried out with the aid of secondary antibodies/FITC (TEBU L 42001) according to the supplier's instructions. Analysis of the samples is carried out by cytometry (FACSCAN cytometry, Cell Quest software; Becton-Dickinson) on the total population. The statistics are performed on 10,000 cells of each sample. The results are expressed as intensity of fluorescence (IF) corresponding to the relative quantity of each marker per cell in a total population of 10,000 cells analyzed.

II. Results:

2.1) Study of CDNA Macroarray:

2.1.1) On Culture of Human Keratinocytes:

| Genes | Control population | Population exposed to the extract | Comparison of control population and population exposed to the extract (in %) |
|---|---|---|---|
| Mn + SOD2 precursor (SOD2) | 1.3 | 3.3 | 244 |
| Cytosolic SOD1 (SOD1) | 4.9 | 6.8 | 138 |

It is observed that the cell population consisting of keratinocytes which is exposed to the extracts of a nonfruiting nonphotosynthetic filamentous bacterium contains significantly more mRNA for SOD2 than the control population whereas the quantity of mRNA for SOD1 is only slightly increased.

2.1.2) On Culture of Human Fibroblasts:

| Gene | Control population | Population exposed to the extract | Comparison of control population and population exposed to the extract (in %) |
|---|---|---|---|
| Mn + SOD2 precursor (SOD2) | 1.9 | 9.3 | 481 |

Just as for the keratinocytes, a cell population consisting of fibroblasts exposed to an extract of a nonfruiting nonphotosynthetic filamentous bacterium contains nearly 5 times more mRNA for SOD2 than the control population.

2.2) PCR Study:

The results below are those obtained on a culture of human keratinocytes.

2.2.1) Results on Cytosolic Superoxide Dismutase 1 (SOD1):

| Treatment | Actin Cycles | SOD1 Cycles | RE* Actin (AU) | RE* SOD1 (AU) | SOD1/ Actin | % Control |
|---|---|---|---|---|---|---|
| Control | 16.12 | 20.12 | 13.99 | 0.93 | 6.64 10-2 | 100 |
|  | 16.13 | 19.96 |  |  |  |  |
| VF Extract | 16.23 | 20.02 | 12.88 | 0.94 | 7.28 10-2 | 110 |
|  | 16.26 | 20.03 |  |  |  |  |

(VF: *Vitreoscilla filiformis*)

These results confirm those observed in point 2.1.1., that is to say that the exposure of a population of keratinocytes to the bacterial extract appeared according to method 3 does not cause transcriptional induction of SOD1.

2.2.2) Results on Mn+Superoxide Dismutase (SOD2):

| Treatment | Actin Cycles | SOD2 Cycles | RE* Actin (AU) | RE* SOD2 (AU) | SOD2/ Actin | % Control |
|---|---|---|---|---|---|---|
| Control | 20.78 | 26.45 | 0.55 | 0.01 | 2.37 10-2 | 100 |
|  | 20.80 | 25.97 |  |  |  |  |
| VF Extract | 20.79 | 23.65 | 0.51 | 0.09 | 1.79 10-2 | 755 |
|  | 21.02 | 23.16 |  |  |  |  |

(VF: *Vitreoscilla filiformis*)

These results also confirm those of point 2.1.1.: the quantity of mRNA encoding SOD2 is much higher in the cell population which was exposed to the bacterial extract.

2.3) Flow Cytometry Study:

The results below are those obtained on a culture of human keratinocytes.

2.3.1) Results on Cytosolic Superoxide Dismutase 1 (SOD1):

Relative quantity of Cu/Zn SOD in control keratinocytes and in keratinocytes treated with the extract (0.1%, W/V) for 24 hours.

| Treatment | IF | Standard Deviation | Number of Sample | % | p |
|---|---|---|---|---|---|
| Control | 180.9 | 15.3 | 3 | 100 | — |
| VF Extract | 217.8 | 7.3 | 3 | 120 | p < 0.01 |

(VF: *Vitreoscilla filiformis*)

It is observed that although exposure to the VF extract does not induce transcription of mRNA for SOD1, its expression is statistically increased (+20%).

2.3.2) Results on Mn Superoxide Dismutase (SOD2):

Relative quantity of MnSOD in control keratinocytes and keratinocytes treated with the extract (0.1%) for 48 hours.

| Treatment | IF | Standard Deviation | Number of Sample | % | p |
|---|---|---|---|---|---|
| Control | 20.2 | 2.6 | 3 | 100 | — |
| VF Extract | 28.1 | 1.8 | 3 | 139 | p < 0.01 |

(VF: *Vitreoscilla filiformis*)

These trials also show an increase in the cellular concentration of SOD2 (+39%) after exposure to the VF extract.

The observation of these trials leads to the conclusion that the fibroblasts exposed in the presence of the extract obtained in Example 1 highly express the messenger RNAs encoding MnSOD (2.1. and 2.2.) and this induction could be confirmed by observing an increase in the protein presence of MnSOD (2.3.), in particular in the mitochondria (visualized by microscopy observations).

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of limiting and/or eliminating objectionable body odors caused by skin lipid oxidation, said method comprising topically administering an effective amount of an extract of a nonfruiting nonphotosynthetic filamentous bacterium in a composition comprising a cosmetically acceptable medium to a subject suffering from objectionable body odors caused by skin lipid oxidation, wherein the effective amount of an extract of a nonfruiting nonphotosynthetic filamentous bacterium is an amount effective to limit and/or eliminate the objectionable body odors.

2. The method of claim 1, wherein the oxidation of skin lipids is caused by colonization of the skin by microorganisms.

3. The method of claim 1 or 2, wherein the extract of a nonfruiting nonphotosynthetic filamentous bacterium is a lipopolysaccharide isolate.

4. The method of claim 1 or 2, wherein the nonfruiting nonphotosynthetic filamentous bacterium is *Vitreoscilla filiformis*.

5. The method of claim 1 or 2, wherein the extract of the nonfruiting nonphotosynthetic filamentous bacterium is combined with at least one antioxidant.

6. The method of claim 5, wherein the antioxidant is lycopene.

7. The method of claim 6, wherein the composition comprises from $10^{-9}$ to 0.1% by weight of pure lycopene relative to the total weight of the composition.

8. The method of claim 1 or 2, wherein the composition comprises in a physiologically acceptable medium, at least one extract of *Vitreoscilla filiformis* and a compound having catalase activity.

9. The method of claim 1 or 2, wherein the composition comprises, in a physiologically acceptable medium, at least one extract of *Vitreoscilla filiformis* and a compound having peroxidase activity.

* * * * *